United States Patent [19]

Monkovic et al.

[11] 4,202,982
[45] May 13, 1980

[54] PROCESS FOR THE PREPARATION OF 14-HYDROXYMORPHINAN DERIVATIVES

[75] Inventors: Ivo Monkovic, Candiac; Carol Bachand, Cote Ste-Catherine; Henry Wong, Candiac, all of Canada

[73] Assignee: Bristol-Myers Company, New York, N.Y.

[21] Appl. No.: 22,669

[22] Filed: Mar. 22, 1979

Related U.S. Application Data

[62] Division of Ser. No. 837,123, Sep. 28, 1977, Pat. No. 4,153,603, which is a division of Ser. No. 669,795, Mar. 23, 1976, Pat. No. 4,058,531.

[51] Int. Cl.² .................. C07D 217/04; C07D 491/04
[52] U.S. Cl. ........................................ 546/89; 546/142
[58] Field of Search ................................. 546/89, 142

[56] References Cited

U.S. PATENT DOCUMENTS

| | | | |
|---|---|---|---|
| 4,013,666 | 3/1977 | Lenz | 546/146 X |
| 4,058,531 | 11/1977 | Monkovic et al. | 546/89 X |
| 4,115,389 | 9/1978 | Monkovic | 546/74 X |
| 4,139,534 | 2/1979 | Lim et al. | 546/74 OR |
| 4,153,603 | 5/1979 | Monkovic et al. | 546/142 OR |

OTHER PUBLICATIONS

Onda et al., Chem. Pharm. Bull., vol. 21, pp. 2359 to 2365 (1973).

*Primary Examiner*—John D. Randolph
*Attorney, Agent, or Firm*—Robert H. Uloth

[57] ABSTRACT

N-substituted-14-hydroxy-3-substituted-morphinan derivatives have been found to possess potent narcotic agonist or antagonist activity. In particular, the compound N-Cyclobutylmethyl-3,14-dihydroxymorphinan has been found to possess potent agonist/antagonist activity as a non-narcotic analgesic. A new and efficient total synthesis of these compounds is described herein from the starting material 2-(p-methoxybenzyl)-1,2,3,4,5,6,7,8-octahydroisoquinoline.

5 Claims, No Drawings

PROCESS FOR THE PREPARATION OF 14-HYDROXYMORPHINAN DERIVATIVES

CROSS-REFERENCE TO RELATED APPLICATION

This application is a divisional of our prior copending application Ser. No. 837,123 filed Sept. 28, 1977, now U.S. Pat. No. 4,153,603, which is a divisional of application Ser. No. 669,795 filed Mar. 23, 1976 (now U.S. Pat. No. 4,058,531).

DESCRIPTION OF THE PRIOR ART

1. U.S. Pat. No. 3,775,414 describes a process for the preparation of the identical compounds prepared by the process claimed herein.

2. U.S. Pat. No. 3,819,635 describes another process for the preparation of the identical compounds prepared by the process claimed herein.

3. Onda et al, Chem. Pharm. Bull. 21, 2359–2365 (1973) report the epoxidation of 1-(p-methoxybenzyl)-2-methyl-1,2,3,4,5,6,7,8-octahydroisoquinoline to produce the two epimeric epoxides

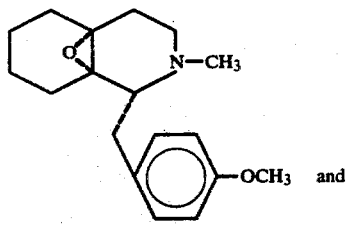

and

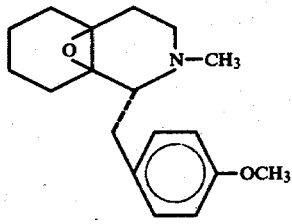

and the diols resulting therefrom having the formulas

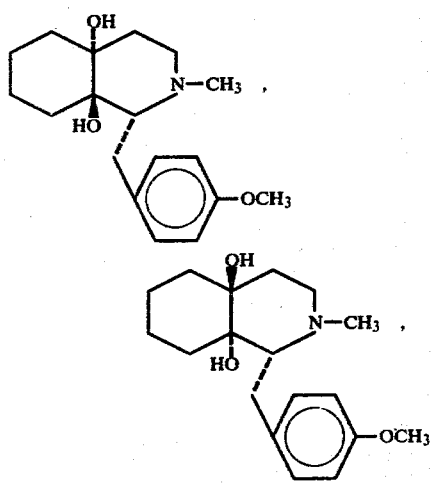

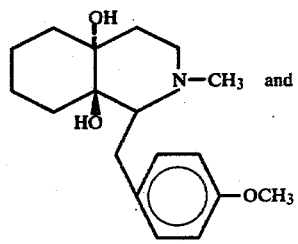

and

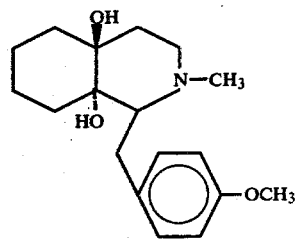

Nothing in this paper describes, anticipates or teaches the preparation of the 9,10-diols in which the N-methyl is alkanoyl as described herein. Furthermore, it is significant that the authors' goal was to synthesize 14-hydroxymorphinans via these diol intermediates and that they failed in their attempts, whereas the instant inventors have succeeded.

4. Schnider and Hellerback, Helv. Chim. Acta., 34, 2218–2222 (1951) describe the preparation of morphinans from the same starting materials as used in the instant invention. Nothing is taught or suggested that 14β-hydroxymorphinans could be prepared via this route.

5. Schnider, Brossi and Vogler, Helv. Chim. Acta., 37, 710–720 (1954) further describe the preparation of 14-deoxymorphinans from the same starting materials as used in the instant invention. Again, nothing is taught or suggested that 14β-hydroxymorphinans could be prepared via this route.

6. Schnider and Hellerback, Helv. Chim. Acta. 33, 1437–1448 (1950) describe the preparation of 14-deoxymorphinans from the same starting materials as used in the instant invention. Again, nothing is taught or suggested that 14β-hydroxymorphinans could be prepared via this route.

7. U.S. Pat. No. 3,919,237 reports the cyclization of compounds having the formulas

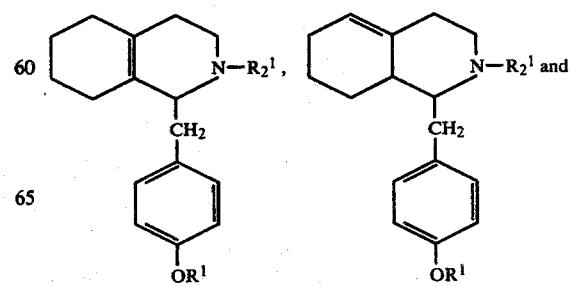

-continued

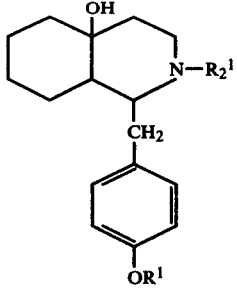

and derivatives thereof into isomorphinans and morphinans using boron trifluoride and a proton/hydronium ion donor as the cyclization catalyst. None of the compounds so produced have a 14β-hydroxy substituent.

SUMMARY OF THE INVENTION

This invention relates to a new process for the preparation of compounds having the formula

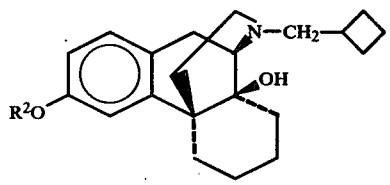

in which $R^2$ is H or (lower)alkyl; or an acid addition salt thereof from the starting material 2-(p-alkoxybenzyl)-1,2,3,4,5,6,7,8-octahydroisoquinoline.

COMPLETE DISCLOSURE

This invention relates to a new and novel synthesis of N-substituted-14-hydroxy-3-substituted-morphinans having the formula

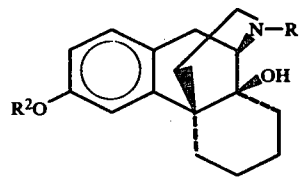

L in which $R^2$ is H or (lower)alkyl and R is cyclobutylmethyl or cyclopropylmethyl.

Drug abuse by thrill-seeking youth or by people looking for an escape from the realities of everyday life has become more and more commonplace in our present society. One class of widely abused drugs are the narcotic analgetics such as codeine, morphine, meperidine, etc. It is because of the high addictive potential of these agents that much time and money are being expended by the pharmaceutical industry and by governments to try and discover and develop new non-addicting analgetics and/or narcotic antagonists.

It was an object of the present invention to develop a method of synthesis for the above-described compounds L that would not be dependent upon opium alkaloids as starting materials and yet would be commercially feasible.

The objectives of the present invention have been achieved by the process of preparing the compounds of Formula L by their total synthesis from the readily available starting material 2-(p-methoxybenzyl)-1,2,3,4,5,6,7,8-octahydroisoquinoline.

The compounds of the instant invention have the basic morphinan nucleus which is numbered and represented by the following plane formula:

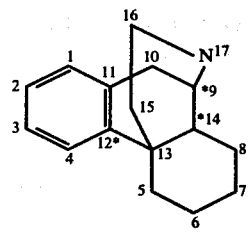

Although there are three asymetric carbons (asterisks) in the morphinan molecule, only two diastereoisomeric (racemic) forms are possible, because the iminoethano system, attached to position 9 and 13, is geometrically contained to a cis(1,3-diaxial)-fusion. These racemates can, therefore, differ only at the junction of rings B and C—in other words, in the configuration of carbon 14. The only variable will be the cis and trans relationship between the 5 (13) and 8 (14) bonds (Analgetics, Ed. George de Stevens, Academic Press, New York, p. 137 (1965)).

When in the compounds of the present invention, the 5 (13) and 8 (14) bonds are cis to each other, we have compounds commonly designated as "morphinans". The use of a graphic representation of a "morphinan" is meant to include the dl racemic mixture and the resolved d and l isomers thereof.

The "morphinan" compounds of the present invention can each exist as two optical isomers, the levorotatory and dextrorotatory isomers. The optical isomers can be graphically illustrated as:

MORPHINANS

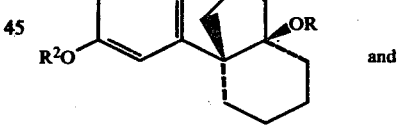

and

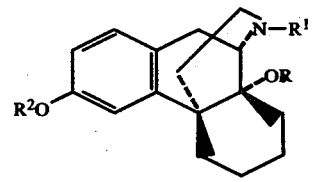

The present invention embodies all of the morphinan isomers including the optical isomers in their resolved form.

The optical isomers can be separated and isolated by fractional crystallization of the diastereoisomeric salts formed, for instance, with d- or l-tartaric acid or D-(+)-α-bromocamphor sulfonic acid. The levo-rotatory isomers of the compounds of the present invention are the most preferred embodiments.

For the purpose of this disclosure, the term "(lower)alkyl" is defined as an alkyl radical containing 1 to 6 carbon atoms. "(Lower)alkenyl" is defined as a hydrocarbon radical of 3 to 7 carbons containing one double bond. The term "(lower)acyl" is an acyl radical of 2 to 6 carbon atoms, e.g., acetyl, propionyl, isobutyryl, etc. The term "pharmaceutically acceptable acid addition salt" is defined to include all those inorganic and organic acid salts of the compounds of the instant invention, which salts are commonly used to produce nontoxic salts of medicinal agents containing amine functions. Illustrative examples would be those salts formed by mixing the compounds of Formula I with hyrochloric, sulfuric, nitric, phosphoric, phosphorous, hydrobromic, maleic, malic, ascorbic, citric or tartaric, pamoic, lauric, stearic, palmitic, oleic, myristic, lauryl sulfuric, naphthalenesulfonic, linoleic or linolenic acid, and the like.

The compounds LV and LX of the instant invention are prepared by a total synthesis comprising 5–6 steps. The synthesis is efficient and appears commercially feasible. The process is outlined in Chart I.

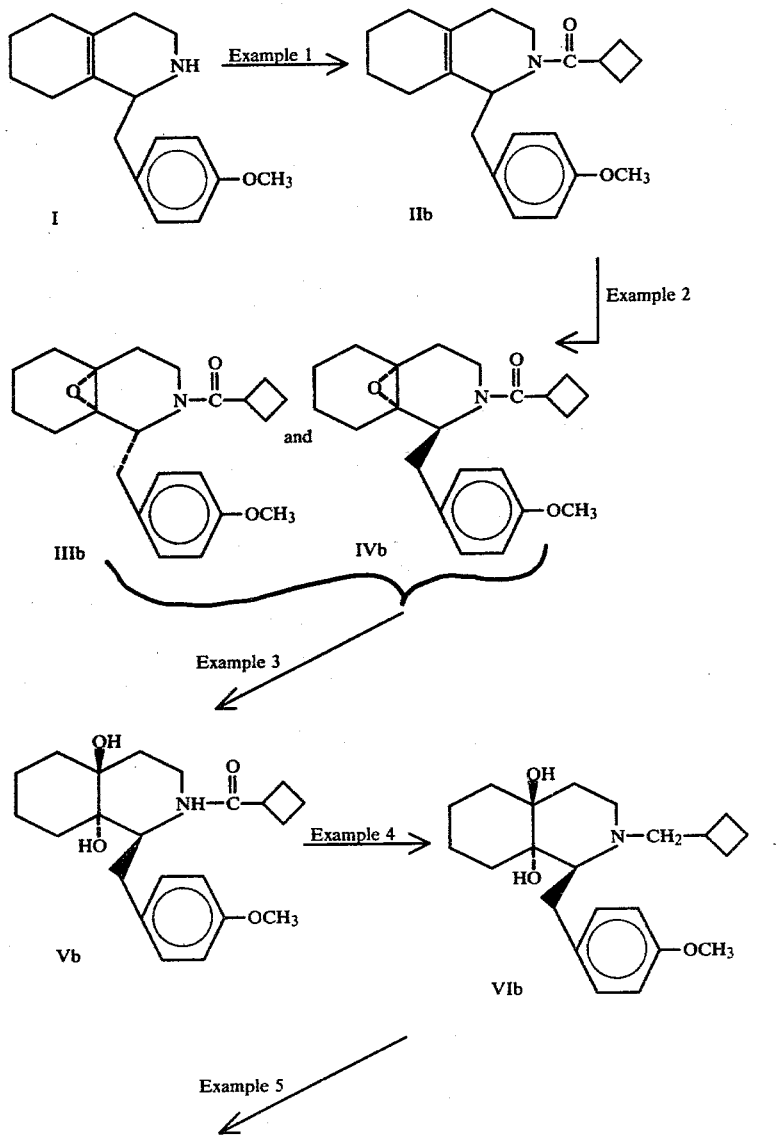

CHART I

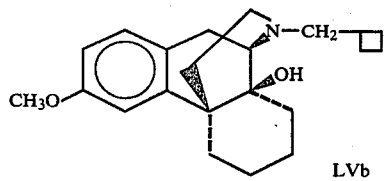
LVb

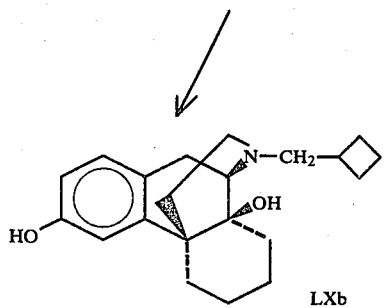
LXb

For the purpose of this disclosure the term "inert organic solvent" means an organic solvent that does not participate in the reaction to the extent that it emerges unchanged from the reaction. Such solvents are methylene chloride, chloroform, dichloroethane, tetrachloromethane, benzene, toluene, ether, ethyl acetate, xylene, tetrahydrofuran dioxane, dimethylacetamide, and the like when an acid halide is employed. When an alkylation reaction is being performed, the inert solvent used may also include (lower)alkanols such as methanol, ethanol, n-propanol, isopropanol and the like.

The term "organic tertiary amine" means a tertiary amine commonly employed as a proton acceptor in alkylation and acylation reactions. Such amines are tri(lower)alkylamines, e.g., trimethylamine, triethylamine and the like, pyridine, dimethylaniline, N-methylpiperidine, and the like.

The compounds N-cyclopropylmethyl-14β-hydroxy-3-methoxymorphinan, N-cyclobutylmethyl-14β-hydroxy-3-methoxymorphinan, N-cyclopropylmethyl-3,14β-dihydroxymorphinan and N-cyclobutylmethyl-3,14β-dihydroxymorphinan are known and described in the processes and examples of U.S. Pat. No. 3,819,635, which issued June 25, 1974.

A preferred embodiment of the present invention is the process for the preparation of the compound having the formula

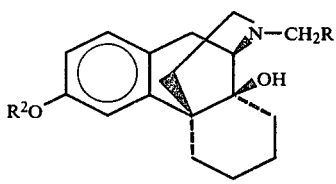
L wherein $R^2$ is H or (lower)alkyl and R is cyclopropyl or cyclobutyl; which process consists of the consecutive steps of (A) treating the compound having the formula

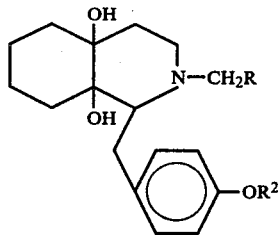
VI in which $R^2$ is (lower)alkyl and R is cyclopropyl or cyclobutyl with borane followed by an acid catalyst to produce the compound having the formula

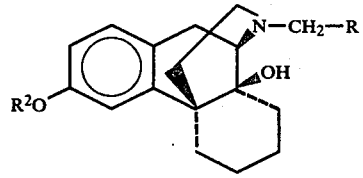
LV in which $R^2$ and R are as defined above; and when desired (B) cleaving the $R^2O$-ether function of compound LV by methods known to the art.

A preferred embodiment of the present invention is the process for the preparation of compounds having the formulas

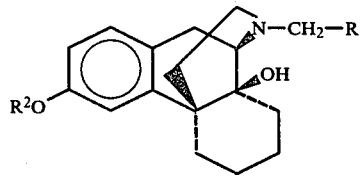
L wherein $R^2$ is H or (lower)alkyl and R is cyclobutyl or cyclopropyl; which process consists of the consecutive steps of (A) treating the compound having the formula

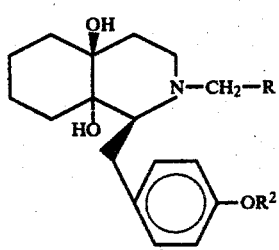

in which R is cyclopropyl or cyclobutyl and $R^2$ is (lower)alkyl with an excess of borane followed by an acid selected from the group consisting of phosphoric, orthophosphoric, pyrophosphoric, polyphosphoric, boron trifluoride etherate and mixtures thereof to produce the compound having the formula

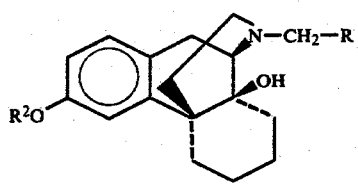

in which $R^2$ is (lower)alkyl; and when desired (B) cleaving the $R^2O$ ether function of compound LV by methods known to the art to produce the compound having the formula

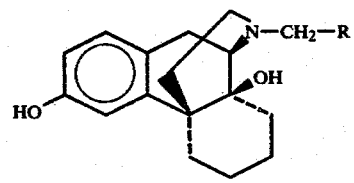

in which R is cyclopropyl or cyclobutyl; and when desired (C) converting compound LX to a nontoxic pharmaceutically acceptable acid addition salt thereof by methods known in the art.

A more preferred embodiment of the present invention is the process for the preparation of compounds having the formula

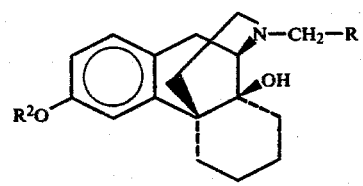

in which $R^2$ is H or $CH_3$ and R is cyclopropyl or cyclobutyl; which process consists of the consecutive steps of (A) treating the compound having the formula

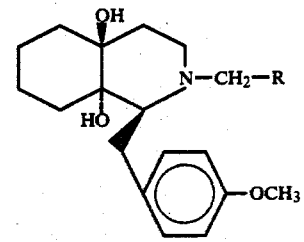

in which R is cyclopropyl or cyclobutyl with a slight molar excess of borane followed by a large excess of concentrated acid selected from the group consisting of phosphoric acid, polyphosphoric acid, orthophosphoric acid, pyrophosphoric acid, boron trifluoride etherate and mixtures thereof with the aid of heat in the range of about 35° C. to 55° C. to produce the compound having the formula

LV

[structure with $CH_3O$]

in which R is as defined above; and when desired (B) treating compound LV with $NaSC_2H_5$, hydrobromic acid, boron tribromide or pyridine hydrochloride to produce the compound having the formula

LX;

[structure with HO]

in which R is cyclopropyl or cyclobutyl; and when desired, (C) converting compound LX into a nontoxic pharmaceutically acceptable acid addition salt thereof by methods known in the art.

The most preferred embodiment of the present invention is the process for the preparation of the compound having the formula

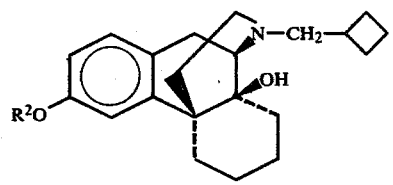

in which $R^2$ is H or $CH_3$; which process comprises the consecutive steps of (A) treating the compound having the formula

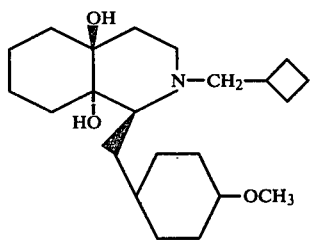

with borane in about a 1:1 molar ratio of borane: VIb in the presence of a large excess of anhydrous phosphoric acid with the aid of heat in the range of about +40° C. to about +50° C. until the cyclization is essentially complete to produce the compound having the formula

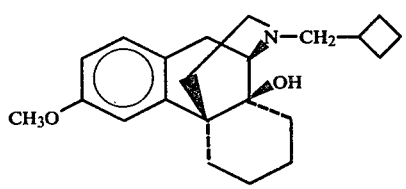

LVb;

and when desired (B) treating compound LVb with $NaSC_2H_5$, hydrobromic acid, boron tribromide or pyridine hydrochloride to produce the compound having the formula

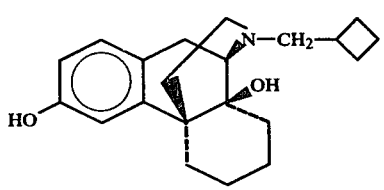

LXb ; and when desired (C) converting compound LXb into a nontoxic pharmaceutically acceptable acid addition salt thereof by methods known in the art.

A preferred embodiment of the present invention is the compound having the formula

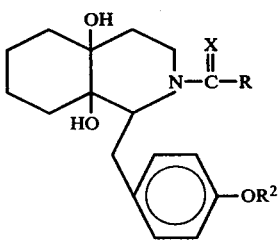

in which X is carbonyl (=O) or $H_2$, $R^2$ is (lower)alkyl of 1 to 5 carbon atoms and R is cyclopropyl or cyclobutyl.

A further preferred embodiment is the compound having the formula

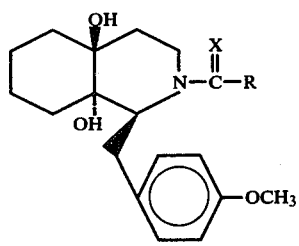

in which X is carbonyl (=O) or $H_2$ and R is cyclopropyl or cyclobutyl.

A most preferred embodiment is the compound having the formula

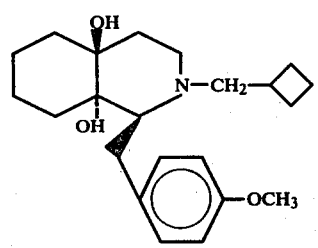

Another preferred embodiment is the compounds having the formulas

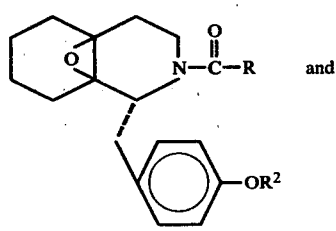

and

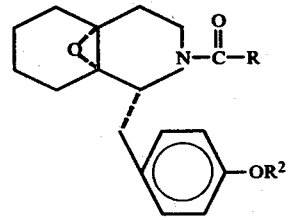

in which $R^2$ is (lower)alkyl of 1 to 5 carbon atoms and R is cyclopropyl or cyclobutyl.

A more preferred embodiment is the compounds having the formulas

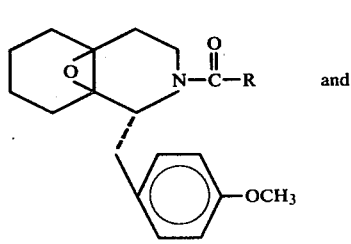

and

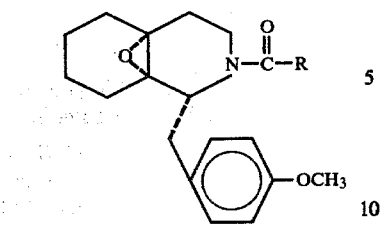

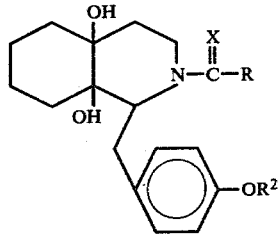

in which R is cyclopropyl or cyclobutyl.

A most preferred embodiment is the compounds having the formula

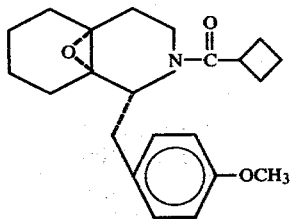

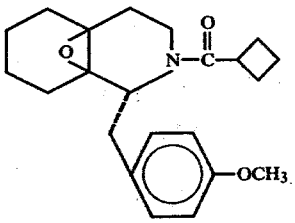

The 9,10-diol compounds of the present invention are capable of existing in different stereochemical forms, e.g.,

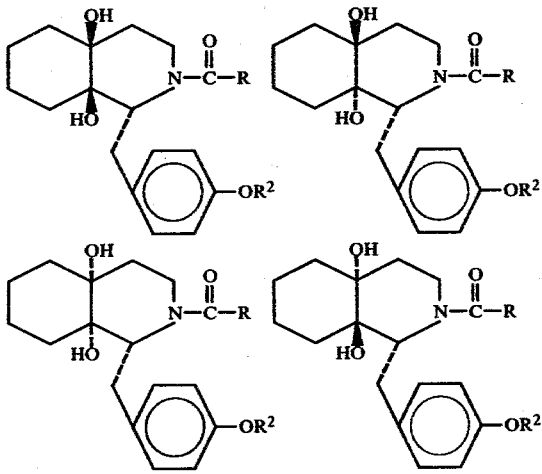

and the four optical isomers thereof. In the synthetic scheme of this process, it is thought that the major product obtained by the opening of the 9,10 epoxide group of compounds IIIb and IVb possesses 9α,10β-diol functions (trans-diols). However, it is thought that some of all the various possible conformations exist in the reaction mixture. The applicants consider all the various diols to be a part of the instant invention and they are so included by reference in the structure illustrated as follows:

EXPERIMENTAL

All temperatures are expressed in degrees Centigrade unless otherwise stated. IR means infrared spectrum, NMR means nuclear magnetic resonance spectrum.

EXAMPLE 1

(±)-2-Cyclobutylcarbonyl-1-(p-methoxybenzyl)-1,2,3,4,5,6,7,8-octahydroisoquinoline (IIb)

To a stirred and cooled (ice-bath) solution of dl-1-(p-methoxybenzyl)-1,2,3,4,5,6,7,8-octahydroisoquinoline I (9.77 g., 37.7 mmol) and triethylamine (4.04 g., 40 mmol) in dichloromethane (80 ml) was added dropwise a solution of cyclobutylcarbonyl chloride (4.76 g., 40 mmol) in dichloromethane (20 ml). The reaction mixture was then washed with water followed by diluted hydrochloric acid and brine. The organic layer was dried and concentrated in vacuo to give 12.8 of racemic IIb as an oil. Molecular weight calculated for $C_{22}H_{29}NO_2$: 339. Found (mass spectrometry): 339.

The (+)-IIb was obtained in a similar procedure from (−)-Ib; $[\alpha]_D = +145°$ (C, 0.1; CHCl$_3$).

A sample for analysis was distilled at 190–200/0.3 mm.

Anal. calc'd. for $C_{22}H_{29}NO_2$: C, 77.84; H, 8.61; N, 4.13. Found: C, 77.58; H, 8.69; H, 4.38.

EXAMPLE 2

(±)-2-Cyclobutylcarbonyl-9,10-epoxy-1-(p-methoxybenzyl)perhydroisoquinolines (IIIb and IVb)

To a cooled (ice-bath) stirred solution of racemic IIb (12.8 g) in dichloromethane (100 ml) was added in several portions m-chloroperbenzoic acid (6.92 g. of 80% purity) and the mixture was left at room temperature for 16 hours. Fifteen ml. of 1 M NaHSO$_3$ in water was added to the solution and shaken vigorously. The mixture was then treated with saturated sodium bicarbonate solution with agitation until the evolution of CO$_2$ ceased. The methylene chloride phase was collected, washed with water and dried over anhydrous sodium sulfate. Filtration and evaporation of the methylene chloride gave 13.2 g of a 4:1 mixture of racemic IIIb and IVb as an oil.

Molecular weight calculated for $C_{22}H_{29}NO_3$: 335. Found (mass spectrometry): 355.

A mixture of (+)-IIIb and (+)-IVb, an oil was obtained from (+)-IIb; $[\alpha]_D = +82°$ (C, 0.1; CHCl$_3$).

A sample for analysis was distilled at 200–205/0.5 mm.

Anal. calc'd. for $C_{22}H_{29}NO_3$: C, 74.33; H, 8.22; N, 3.94. Found: C, 74.13; H, 8.40; N, 3.76.

A sample of pure IIIb was obtained by column chromatography (silica gel-ether) as white solid; m.p. 109°–110° (from ether); $[\alpha]_D = +70.5$ (C. 05, CHCl$_3$).

EXAMPLE 3

(±)-2-Cyclobutylcarbonyl-9α,10β-dihydroxy-1β-(p-methoxybenzyl)-perhydroisoquinoline (Vb)

To a cooled (ice-bath) solution of a mixture of racemic IIIb and IVb (1.7 g.) in THF [Tetrahydrofuran, 25 ml] was added 15% aqueous perchloric acid (20 ml) and the mixture allowed to stand at room temperature for 16 hours. It was then treated with an ice-cold solution of sodium carbonate (30 ml of 10% solution) and extracted with benzene (2×20 ml). The extract was dried and evaporated in vacuo to give an oil, which crystallized from ether. There was obtained 920 mg. of racemic Vb as white solid: m.p. 135°–137°. Recrystallization from ether gave an analytical sample; m.p. 148°–150° C.

Anal. calc'd. for $C_{21}H_{31}NO_4$: C, 70.75; H, 8.37; N, 3.75. Found: C, 71.12; H, 8.16; N, 3.97.

The optically active Vb was obtained similarly from pure (+)-IIIb as white solid, m.p. 130°–132° from acetonitrile, $[\alpha]_D = -4.0$ (C, 0.4, $CHCl_3$).

EXAMPLE 4

(±)-2-Cyclobutylmethyl-9α,10β-dihydroxy-1β-(p-methoxybenzyl)-perhydroisoquinoline (VIb)

To a boiling solution of lithium aluminum hydride (300 mg) in THF (8 ml) was added dropwise a solution of 920 mg of racemic Vb in THF (20 ml) and the mixture was heated under reflux for 3 hours. After cooling, the excess lithium aluminum hydride was decomposed by the careful addition of about 0.5 ml of water, followed by filtration and evaporation in vacuo to give 800 mg. of racemic solid VIb; m.p. 120°–122° C.

Molecular weight calculated for $C_{22}H_{33}NO_3$: 359. Found (mass spectrometry): 359.

The optically active VIb was similarly obtained from (−)-Vb; m.p. 136° C., 137° C. from 2-propanol; $[\alpha]_D = -42°$ (C, 0.53; $CHCl_3$).

Anal. Calc'd. for $C_{21}H_{33}NO_3$, C, 73.50; H, 9.25; N 3.90. Found: C, 73.25; H, 9.49; N, 3.90.

EXAMPLE 5

(±)-N-Cyclobutylmethyl-14β-hydroxy-3-methoxymorphinan (LVb)

To a cooled (ice-bath) solution of VIb (800 mg) in benzene (10 ml) was added 1 M borane solution in THF (2.2 ml) and the mixture concentrated in vacuo. To the solid borane complex was added phosphoric acid (16 g., anhydrous) and the mixture was heated at 45° for 16 hours. It was then treated with water (60 ml) and concentrated ammonium hydroxide (24 ml) and extracted with benzene (2×20 ml). The benzene extract was dried and concentrated in vacuo to give 600 mg. of crude racemic LVb as an oil. This was dissolved in acetone and treated with dry hydrogen chloride solution in ether to give 500 mg of solid hydrochloride salt of LVb; m.p. 248°–250° C. Reported m.p.: 248°–250° C. The optically active LVb was similarly obtained purified as free base by recrystallization from methanol; m.p. 82°–84° C. $[\alpha]_D = +81.0$ (C, 0.7; MeOH).

If (+)-I is utilized as starting material, then the end product LVb would be levorotatory.

EXAMPLE 6

(±)-2-Cyclopropylcarbonyl-1-(p-methoxybenzyl)-1,2,3,4,5,6,7,8-octahydroisoquinoline (IIc)

Substitution in the procedure of Example 1 for the cyclobutylcarbonyl chloride used therein of an equimolar quantity of cyclopropylcarbonyl chloride produces the title product IIc.

EXAMPLE 7

(±)-2-Cyclopropylcarbonyl-9,10-epoxy-1-(p-methoxybenzyl)perhydroisoquinolines (IIIc and IVc)

Substitution in the procedure of example 2 for the racemic IIb used therein of an equimolar quantity of IIc produces the title compounds IIIc and IVc.

EXAMPLE 8

(±)-2-Cyclopropylcarbonyl-9α,10β-dihydroxy-1β-(p-methoxybenzyl)perhydroisoquinoline (Vc)

Substitution in the procedure of example 3 for the racemic IIIb and IVb used therein of an equimolar quantity of IIIc and IVc produces the title compound Vc.

EXAMPLE 9

(±)-2-Cyclopropylmethyl-9α,10β-dihydroxy-1β-(p-methoxybenzyl)perhydroisoquinoline (VIc)

Substitution in the procedure of Example 4 for the racemic Vb used therein of an equimolar quantity of Vc produces the title compound VIc.

EXAMPLE 10

(±)-N-Cyclopropylmethyl-14β-hydroxy-3-methoxymorphinan (LVc)

Substitution in the procedure of Example 5 for the racemic VIb used therein of an equimolar quantity of VIc produces the title product LVc.

EXAMPLE 11

(±)-2-Cyclobutylmethyl-9α, 10β-dihydroxy-'β(p-methoxy benzyl)perhydroisoquinoline (VIb)

To a cooled (ice-bath) stirred solution of racemic IIb (12.8 g) in 100 ml of formic acid, was added in several portions a slight molar excess of performic acid. The mixture was heated at 40°–50° C. for several hours and cooled to room temperature. Fifteen ml. of 1 M $NaHSO_3$ in water was added and shaken. The solution was diluted with 5 to 8 volumes of water and extracted with several 100 ml portions of methylene chloride. The methylene chloride extracts were combined, washed with water and then treated with saturated sodium bicarbonate solution until the evolution of $CO_2$ ceased. The methylene chloride solution was collected, dried over anhydrous $Na_2SO_4$, filtered and evaporated in vacuo to yield a mixture of product which was directly reduced as in Example 4 to give VIb after crystallization from propanol; m.p. 120°–122° C.

We claim:

1. The compound having the formula

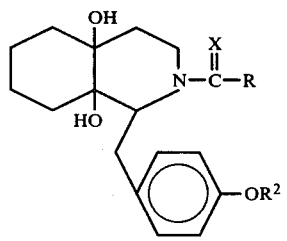

in which X is carbonyl (=O), $R^2$ is (lower)alkyl of 1 to 5 carbon atoms and R is cyclopropyl or cyclobutyl.

2. The compound of claim 1 having the formula

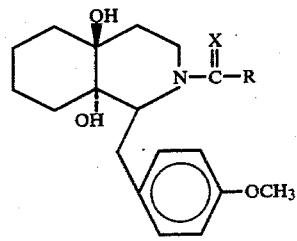

in which X is carbonyl (=O) and R is cyclopropyl or cyclobutyl.

3. The compounds having the formulas

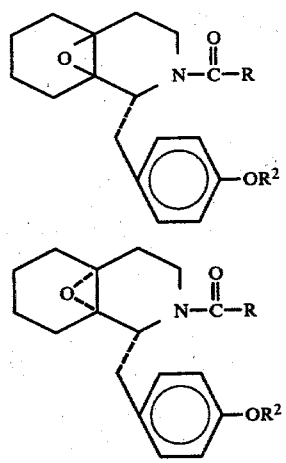

in which $R^2$ is (lower)alkyl of 1 to 6 carbon atoms and R is cyclopropyl or cyclobutyl.

4. The compounds of claim 3 having the formulas

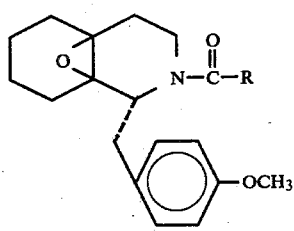

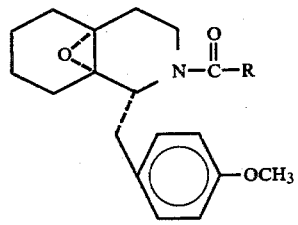

in which R is cyclopropyl or cyclobutyl.

5. The compounds having the formula

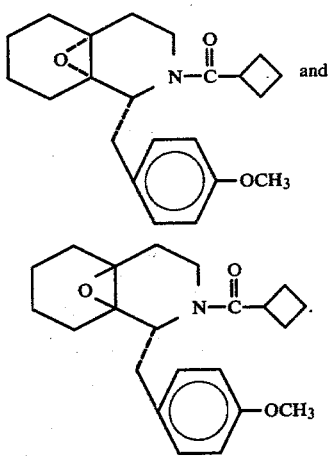

* * * * *